United States Patent
Sato et al.

(10) Patent No.: US 10,597,606 B2
(45) Date of Patent: Mar. 24, 2020

(54) PRODUCTION METHOD OF MARINE PRODUCT-DERIVED FREE MONOUNSATURATED FATTY ACIDS OR LOWER ALCOHOL ESTERS THEREOF

(71) Applicant: NIPPON SUISAN KAISHA, LTD., Tokyo (JP)

(72) Inventors: Seizo Sato, Hachiojo (JP); Takuro Fukae, Hachiojo (JP); Naomi Ohtsuka, Hachiojo (JP); Hideaki Yamaguchi, Hachiojo (JP)

(73) Assignee: Nippon Suisan Kaisha, Ltd., Tokyo (JP)

( * ) Notice: Subject to any disclaimer, the term of this patent is extended or adjusted under 35 U.S.C. 154(b) by 0 days.

(21) Appl. No.: 15/393,576

(22) Filed: Dec. 29, 2016

(65) Prior Publication Data
US 2017/0107453 A1  Apr. 20, 2017

Related U.S. Application Data

(63) Continuation of application No. PCT/JP2015/069090, filed on Jul. 2, 2015.

(30) Foreign Application Priority Data

Jul. 2, 2014 (JP) ................... 2014-136436

(51) Int. Cl.
*C11C 1/04* (2006.01)
*C11C 1/10* (2006.01)
*C11C 3/10* (2006.01)
*A23L 33/12* (2016.01)
*A61K 31/201* (2006.01)
*A61K 31/231* (2006.01)
*C11C 3/04* (2006.01)

(52) U.S. Cl.
CPC ............... *C11C 1/04* (2013.01); *A23L 33/12* (2016.08); *A61K 31/201* (2013.01); *A61K 31/231* (2013.01); *C11C 1/10* (2013.01); *C11C 3/04* (2013.01); *C11C 3/10* (2013.01); *A23V 2002/00* (2013.01)

(58) Field of Classification Search
CPC ..... C11C 1/04; C11C 1/10; C11C 3/04; C11C 3/10; A23L 33/12; A61K 31/201; A61K 31/231
See application file for complete search history.

(56) References Cited

U.S. PATENT DOCUMENTS

| | | | |
|---|---|---|---|
| 3,764,358 A | 10/1973 | Papalos et al. | |
| 4,601,856 A | 7/1986 | Suzuki et al. | |
| 5,840,944 A | 11/1998 | Furihata et al. | |
| 2004/0028691 A1* | 2/2004 | Antoku | A61K 31/232 424/184.1 |
| 2010/0113387 A1 | 5/2010 | Loftsson et al. | |
| 2014/0066508 A1* | 3/2014 | Yang | A61K 31/201 514/560 |

FOREIGN PATENT DOCUMENTS

| | | | |
|---|---|---|---|
| GB | 2217173 A | 10/1989 | |
| JP | S61-297 A | 1/1986 | |
| JP | 61-210048 A | 9/1986 | |
| JP | S61-291540 A | 12/1986 | |
| JP | S64-48898 A | 2/1989 | |
| JP | 09-278706 A | 10/1997 | |
| JP | H09-279179 A | 10/1997 | |
| JP | 2001-294525 A | 10/2001 | |
| JP | WO 2012121080 A1 * | 9/2012 | ........... A61K 31/201 |
| WO | WO 89/08095 A1 | 9/1989 | |
| WO | WO 2008/133573 A1 | 11/2008 | |
| WO | WO 2012/121080 A1 | 9/2012 | |

OTHER PUBLICATIONS

Elementis: A comparison of Meadowfoam Seed Oil and Jojoba Oil. (Year: 2011).*
Sigma Aldrich cis-11-eicosenoic acid product page. Published 2012. (Year: 2012).*
Ossia et al (Journal of Mechanical Science and Technology vol. 22 pp. 1527-1536, published 2008) (Year: 2008).*
Apelblat et al (Journal of American Oil Chemists vol. 73 pp. 239-244 published 1996) (Year: 1996).*
Ranhotra and coworkers (Cereal Chemistry vol. 63 pp. 459-461 published 1986). (Year: 1986).*
Moffat, C.F., et al (Proceedings of the Nutrition Society vol. 52 pp. 441-456 published 1993). (Year: 1993).*
Borgstrom et al (Fish as Food vol. 1 pp. 215-216 published 1961) (Year: 1961).*
Toyama and Tsuchiya (Journal of the Society of Chemical Industry Japan vol. 37 pp. 14B-21B, published 1934) (Year: 1934).*
Supplementary European Search Report dated Oct. 30, 2017, in EP 15815644.8.

(Continued)

*Primary Examiner* — Timothy P Thomas
*Assistant Examiner* — George W Kosturko
(74) *Attorney, Agent, or Firm* — Foley & Lardner LLP

(57) ABSTRACT

A method for producing monovalent unsaturated free fatty acids having 20 and/or 22 carbons or low-grade alcohol esters thereof, said method involving the following: obtaining free fatty acids or low-grade alcohol esters through the hydrolysis or alcoholysis of oils and fats derived from marine products; carrying out distillation on the free fatty acids or low-grade alcohol esters, and reducing the concentration of fatty acids with 18 or less carbons in the low-grade alcohol esters or free fatty acids; and collecting fractions of monovalent unsaturated free fatty acids having 20 and/or 22 carbons or low-grade alcohol esters thereof by column chromatography based on reversed-phase distribution.

8 Claims, No Drawings

(56) References Cited

OTHER PUBLICATIONS

Yang et al., "Dietary Saury Oil Reduces Hyperglycemia and Hyperlipidemia in Diabetic KKAy Mice and in Diet-Induced Obese C57BU6J Mice by Altering Gene Expression," Lipids, Apr. 5, 2011, 46(5):425-434.

International Search Report and Written Opinion dated Sep. 29, 2015, in PCT/JP2015/069090.

JOCS Standard Methods for the Analysis of Fats. Oils and Related Materials,' 2013 Edition, 2.4.2.1-2013, 4 pages, with English translation, 5 pages.

JOCS Standard Methods for the Analysis of Fats, Oils and Related Materials, 2013 Edition, 2.4.2.2-2013, 4 pages, with English translation, 5 pages.

Yang et al., "Dietary Saury Oil Reduces Hyperglycemia and Hyperlipidemia in Diabetic KKAy Mice and in Diet-Induced Obese C57BL/6J Mice by Altering Gene Expression," Lipids, 2011, 46:425-434.

Yang et al., "Beneficial Effects of Dietary Fish-Oil-Derived Monounsaturated Fatty Acids on Metabolic Syndrome Risk Factors and Insulin Resistance in Mice," J. Agric. Food Chem., 2011, 59:7482-7489.

Yang et al., "Pollock oil supplementation modulates hyperlipidemia and ameliorates hepatic steatosis in mice fed a high-fat diet," Lipids in Health and Disease, 2011, 10:189, 1-10.

Office Action dated Jul. 19, 2018, in Australian patent application No. 2015285212.

Sahena et al., "PUFAs in Fish: Extraction, Fractionation, Importance in Health," Comprehensive Reviews in Food Science and Food Safety, 2009, 8:59-74.

\* cited by examiner

PRODUCTION METHOD OF MARINE PRODUCT-DERIVED FREE MONOUNSATURATED FATTY ACIDS OR LOWER ALCOHOL ESTERS THEREOF

TECHNICAL FIELD

The present invention relates to a production method of free monounsaturated fatty acids having not less than 20 carbons (unsaturated fatty acids having one double bond; also called "MUFAs" hereinafter) or lower alcohol esters thereof, free monounsaturated fatty acids or lower alcohol esters thereof, and applications thereof.

BACKGROUND ART

Polyunsaturated fatty acids ("PUFAs" hereinafter) such as eicosapentaenoic acid ("EPA" hereinafter) and docosahexaenoic acid ("DHA" hereinafter), which are fatty acids unique to fish oil, have been found to have a great deal of bioactivity and are widely used as dietary supplements and medicaments.

Vegetable oils are widely used in foodstuffs, and have gained attention because oleic acid (degree of unsaturation 1), linoleic acid (degree of unsaturation 2), and linolenic acid (degree of unsaturation 3), which are unsaturated fatty acids having 18 carbons contained in large quantities in vegetable oils, reduce cholesterol levels, whereas saturated fatty acids increase blood cholesterol levels. Oleic acid, which is a MUFA having 18 carbons, is said to be particularly good for health because it reduces only bad cholesterol without affecting good cholesterol. Vegetable oils also contain MUFAs having 20 or 22 carbons, which are contained in large quantities in canola oil, Matthiola oil, mustard oil, tung oil, and the like. A MUFA having not less than 20 carbons is mainly called an LC-MUFA. As production methods of vegetable oil-derived LC-MUFAs, methods such as urea addition, and recrystallization, have been reported (for example, WO/89/08095 and Japanese Unexamined Patent Application Publication No. H9-278706 A).

Fish oils also contain monounsaturated fatty acids ("MUFAs" hereinafter), mainly MUFAs having 20 or 22 carbons (a MUFA having at least 20 carbons is called an "LC-MUFA" hereinafter). Fish oil-derived LC-MUFAs have been reported to have bioactivity such as a cholesterol-reducing action (for example, WO/2012/121080). Vegetable oil-derived LC-MUFAs are mainly n-9, whereas fish oil-derived LC-MUFAs are mainly n-11. n-9 indicates that the 9th bond from the methyl terminal of the fatty acid is a double bond, and n-11 indicates that the 11th bond from the methyl terminal of the fatty acid is a double bond.

Unlike vegetable oils, oils and fats derived from marine products contain many types of fatty acid having from 12 to 24 carbons and 0 to 6 double bonds in addition to MUFAs. As an example of refinement from marine product oils and fats, WO/2012/121080 describes a method for purification on a laboratory scale in which saury oil is subjected to ethyl esterification and applied to an ODS column to concentrate MUFAs. The concentration of marine product-derived MUFAs having 20 and/or 22 carbons obtained by this method has been shown to be approximately 70%.

SUMMARY OF INVENTION

Technical Problem

Among the many types of fatty acids having from 12 to 24 carbons and from 0 to 6 double bonds other than MUFAs contained in marine product-derived oils and fats, there are fatty acids that exhibit behavior resembling that of MUFAs in the refinement process. Therefore, it is not easy to efficiently concentrate MUFAs in high concentrations, and up to now there have been no examples of mass production by an industrially practicable method.

LC-MUFAs, which are richly contained in fats and oils of marine products such as saury and cod, are reported to have an ameliorating effect on metabolic syndrome, but marine product oils and fats also contain polyunsaturated fatty acids having not less than 20 carbons (also called "LC-PUFAs" hereinafter), and they have been a hindrance to accurate verification of the effect of LC-MUFAs and esters thereof. To clinically apply LC-MUFAs or esters thereof or the like that are effective as medicaments or to apply them to a wider range of diseases, those containing LC-MUFAs in high concentration or those containing substantially no components other than LC-MUFAs, for example, those in which the LC-MUFA concentration (purity) is not less than 85% by weight, and further, not less than 90% by weight, must be produced in large quantities with high efficiency.

In particular, LC-MUFAs derived from marine product oils and fats have, as main components, isomers in which the position of the double bond differs from that of LC-MUFAs contained in oils and fats derived from vegetable oils. Since high-concentration LC-MUFAs derived from marine product oils and fats do not exist, a means of supplying marine product oil- and fat-derived LC-MUFAs containing such isomers in high concentration is required.

An object of the present invention is to provide an industrial production method for efficiently obtaining high-concentration LC-MUFAs, or for efficiently obtaining LC-MUFAs in which the contents of LC-PUFAs and saturated fatty acids are low, and high-purity LC-MUFAs obtained thereby.

Solution to Problem

The present invention includes the following aspects of methods for producing monounsaturated fatty acids or lower alcohol esters thereof having 20 and/or 22 carbons, and monounsaturated fatty acids or lower alcohol esters thereof having 20 and/or 22 carbons.

[1] A production method of free monounsaturated fatty acids or lower alcohol esters thereof having 20 and/or 22 carbons, the method comprising: hydrolyzing or alcoholizing a marine product raw material-derived oil and/or fat, to obtain free fatty acids or lower alcohol esters thereof; distilling the free fatty acids or lower alcohol esters thereof, and reducing a concentration of fatty acids having not more than 18 carbons in the free fatty acids or lower alcohol esters thereof; and fractionating fractions of free monounsaturated fatty acids or lower alcohol esters thereof having 20 and/or 22 carbons by reverse phase distribution column chromatography.

[2] The method according to [1], wherein the marine product raw material-derived oil and/or fat is a refined oil obtained by at least one refinement process selected from the group consisting of degumming, deacidification, decoloration, and deodorizing.

[3] The method according to [1] or [2], wherein the distillation is rectification.

[4] The method according to [1] or [2], wherein the distillation is molecular distillation or short path distillation.

[5] The method according to any one of [1] to [3], wherein the distillation is rectification using structured packing.

[6] The method according to any one of [1] to [5], wherein the free monounsaturated fatty acids or lower alcohol esters thereof having 20 and/or 22 carbons obtained by column chromatography has a concentration in all fatty acids of not less than 70% by weight, not less than 80% by weight, not less than 90% by weight, or not less than 95% by weight.

[7] The method according to any one of [1] to kit wherein a concentration of free fatty acids or lower alcohol esters thereof having not more than 18 carbons after distillation is not greater than 30% by weight, not greater than 20% by weight, not greater than 10% by weight, not greater than 5% by weight, or not greater than 1% by weight in all fatty acids.

[8] The method according to any one of [1] to [7], wherein a concentration of free polyunsaturated fatty acids or lower alcohol esters thereof after distillation and column chromatography is not greater than 5% by weight or not greater than 1% by weight in all fatty acids.

[9] Free monounsaturated fatty acids or lower alcohol esters thereof having 20 and/or 22 carbons obtainable by the method described in any one of [1] to [8].

[10] Free fatty acids or lower alcohol esters thereof comprising: free monounsaturated fatty acids or lower alcohol esters thereof having 20 and/or 22 carbons which contains at least free gadoleic acid (n-11) or a lower alcohol ester thereof or free cetoleic acid (n-11) or a lower alcohol ester thereof in a concentration of not less than 70% by weight, not less than 80% by weight, or not less than 90% by weight in all fatty acids.

[11] The free fatty acids or lower alcohol esters thereof according to [10], wherein the free monounsaturated fatty acid or lower alcohol ester thereof having 20 carbons is free gadoleic acid (n-11) or a lower alcohol ester thereof and/or free gondoic acid (n-9) or a lower alcohol ester thereof, and the free monounsaturated fatty acid or lower alcohol ester thereof having 22 carbons is free cetoleic acid (n-11) or a lower alcohol ester thereof and/or free euricic acid (n-9) and a lower alcohol ester thereof.

[12] Free fatty acids or lower alcohol esters thereof, comprising free monounsaturated fatty acids or lower alcohol esters thereof having 20 and/or 22 carbons which contain at least free gadoleic acid or a lower alcohol ester thereof or free cetoleic acid or a lower alcohol ester thereof in a concentration of at least 70% by weight in all the fatty acids; free saturated fatty acids or lower alcohol esters thereof in a concentration of not greater than 10% by weight in all the fatty acids; and free polyunsaturated fatty acids or lower alcohol esters thereof in a concentration of not greater than 5% by weight in all the fatty acids.

[13] The free fatty acids or lower alcohol esters thereof according to [12], wherein the free monounsaturated fatty acids or lower alcohol esters thereof having 20 and/or 22 carbons have a concentration of at least 90% by weight in all the fatty acids, and contain at least free gadoleic acid or a lower alcohol ester thereof or free cetoleic acid or a lower alcohol ester thereof, the free saturated fatty acids or lower alcohol esters thereof have a concentration of not greater than 5% by weight in all the fatty acids, and the free polyunsaturated fatty acids or lower alcohol esters thereof have a concentration of not greater than 1% by weight in all the fatty acids.

[14] The free fatty acids or lower alcohol esters thereof according to any one of [9] to [13], wherein the acids or esters comprise at least free gadoleic acid or a lower alcohol ester thereof, and the free gadoleic acid (n-11) or a lower alcohol ester thereof has a concentration of not less than 30% by weight, not less than 40% by weight, not less than 50% by weight, not less than 60% by weight, or not less than 70% by weight in all the fatty acids.

[15] The free fatty acids or lower alcohol esters thereof according to any one of [9] to [14], comprising free fatty acids or lower alcohol esters thereof having not more than 18 carbons in a concentration of not greater than 30% by weight, not greater than 20% by weight, not greater than 10% by weight, not greater than 5% by weight, or not greater than 1% by weight in all the fatty acids.

[16] The free fatty acids or lower alcohol esters thereof according to any one of [9] to [15], wherein the acids or esters are obtainable from an oil and/or fat of a marine product.

[17] Use of the free fatty acids or lower alcohol esters thereof described in any one of [9] to [16] in production of a foodstuff.

[18] A metabolic syndrome ameliorating agent or a lifestyle-related disease preventing agent comprising the free fatty acids or lower alcohol esters thereof described in any one of [9] to [16] as an active ingredient.

[19] A metabolic syndrome ameliorating composition or a lifestyle-related disease preventing composition comprising the metabolic syndrome ameliorating agent or lifestyle-related disease preventing agent described in [18] and an additive.

[20] Use of the free fatty acids or lower alcohol esters thereof described in any one of [9] to [16] in production of the metabolic syndrome ameliorating composition or lifestyle-related disease preventing composition described in [18].

Advantageous Effects of Invention

According to the method of the present invention, high-concentration LC-MUFAs can be efficiently obtained. Furthermore, according to an aspect of the present invention, LC-MUFAs derived from oils and fats of marine products in which the contents of LC-PUFAs and saturated fatty acids are low, can be obtained in high concentration with high efficiency. According to an aspect of the present invention, the content of saturated fatty acids and LC-PUFAs in a composition of LC-MUFAs can be reduced. When LC-MUFAs are utilized as a functional component, they are suitable for use in applications that demand low concentrations of saturated fatty acids and/or LC-PUFAs. When the number of carbons or the number of double bonds of fatty acids differ, major differences occur not only in their physical properties but in their physiological functions as well. By separating marine product fat and oil-derived LC-MUFAs, which was difficult to do in the past, according to the number of carbons, it is possible to clarify the functions of each and to use them effectively. LC-MUFAs are suitable for applications such as medicaments and dietary supplements.

DESCRIPTION OF EMBODIMENTS

The terms "oil" and "oil and/or fat" in the present specification include not only triglycerides, but also include crude oils comprising triglycerides as a main component and other lipids such as diglycerides, monoglycerides, phospholipids, cholesterol, and free fatty acids. "Oil" and "oil and/or fat" mean compositions containing these lipids.

The term "fatty acid" not only indicates a free saturated or unsaturated fatty acid itself, but also includes fatty acids contained as constituent units in free saturated or unsaturated fatty acids, saturated or unsaturated fatty acid alcohol esters, triglycerides, diglycerides, monoglycerides, phospholipids, steryl esters, and the like, which can also be called constituent fatty acids. In this specification, unless specified otherwise, the forms of compounds containing fatty acids may be omitted. Examples of forms of compounds containing fatty acids include a free fatty acid form, a fatty acid alcohol ester form, a glycerol ester form, a phospholipid form, a steryl ester form, and the like. Compounds containing the same fatty acids may be contained in a single form or may be contained as a mixture of two or more forms in the oil.

It has been empirically determined that the reaction efficiency of hydrolysis or alcoholysis of fatty acids is high, and after hydrolysis or alcoholysis, a composition containing mainly fatty acid forms of free fatty acids or lower alcohol esters thereof is obtained. For this reason, unless otherwise specified, fatty acids after the processing step are denoted while omitting that they are a composition or that the free fatty acid is of a free fatty acid form or a lower alcohol ester form. However, this does not completely negate the fact that fatty acids of a form other than a free fatty acid form or a lower alcohol ester form are included.

When denoting fatty acids, a numerical expression may be used, whereby the number of carbons, the number of double bonds, and the locations of double bonds are each expressed in a simplified manner using numbers and alphabets, respectively. For example, a saturated fatty acid having 20 carbons may be denoted as "C20:0". A monounsaturated fatty acid having 18 carbons may be denoted as "C18:1" or the like. Arachidonic acid may be expressed as "C20:4, n-6" or the like. "n-" indicates the position of the double bond counted from the methyl terminal of the fatty acid. For example, "n-6" indicates that the position of the double bond is the 6th position counting from the methyl terminal of the fatty acid. This method is known to those of ordinary skill in the art, and those of ordinary skill in the art can easily specify fatty acids expressed in accordance with this method.

In the present specification, the term "crude oil" means a mixture of the lipids described above, and means an oil in the state obtained by extraction from an organism. In the present specification, the term "refined oil" means an oil from which substances, such as phospholipids and cholesterol, other than the target substance have been removed by performing at least one oil and fat refining process selected from the group consisting of a degumming process, a deacidification process, a decoloring process, and a deodorizing process.

In the present invention, examples of "oil and fat obtained from marine products" or "oil and/or fat derived from marine product raw material" are lipids containing oils and fats, phospholipids, wax esters, and the like contained in fish, shellfish, or marine animals. Examples of fish with a high content of LC-MUFAs include fish of the saury family such as Pacific saury; fish of the cod family such as Pacific cod, Alaska pollock, Atlantic cod, and sablefish; fish of the Salmonidae family such as chum salmon, coho salmon, sockeye salmon, pink salmon, oncorhynchus, and rainbow trout; fish of the Osmeridae family such as capelin and shishamo smelt; and fish of the Clupeidae family such as herring. A relatively large amount of LC-MUFAs is also contained in fish such as sand lance, tuna, mackerel, splendid alfonsino, gnomefish, red rockfish, Pacific ocean perch, and *Sebastes iracundus*. A large amount of LC-MUFAs is also contained in liver oil of sharks such as spiny dogfish, basking shark, and silver chimaera. Oils and fats derived from animals such as seals and whales may also be used. A raw material that does not contain a large quantity of LC-MUFAs may be also used by concentration.

The Standard Tables of Food Composition in Japan Fifth Revised Edition states that fatty acids in saury (raw) contain 19.3% by weight of docosenoic acid (C22:1) and 17.2% by weight of icosenoic acid (C20:1), and the total amount of monounsaturated fatty acids is 50.1% by weight. Saury oil is characterized by having a larger content of monounsaturated fatty acids among fish oils. It is preferable to select fish oils containing not less than 10% by weight and preferably not less than 15% by weight of docosenoic acid and icosenoic acid. Fish oils of fish species caught in large quantities such as saury and cod are suitable as raw materials.

In the present invention, "monounsaturated fatty acid" or "MUFA" indicates a fatty acid having one double bond, and "polyunsaturated fatty acid" or "PUFA" indicates a fatty acid having not less than four double bonds. A long-chain fatty acid having not less than 20 carbons that is a MUFA or PUFA is denoted as "LC-MUFA" or "LC-PUFA."

Among LC-MUFAs, MUFAs having 20 and/or 22 carbons, especially n-11 isomers, can be obtained in high concentration in the present invention.

A MUFA having 20 carbons is called eicosenoic acid (icosenoic acid) in IUPAC nomenclature, and depending on the position of the double bond, it is called cis-icos-9-enoic acid (n-11, common name gadoleic acid), cis-icos-11-enoic acid (n-9, common name gondoic acid), and the like. A MUFA having 22 carbons is called docosenoic acid in IUPAC nomenclature, and depending on the position of the double bond, it is called cis-docos-11-enoic acid (n-11, common name cetoleic acid), cis-docos-13-enoic acid (n-9, common name euricic acid), and the like. Marine product oils and fats contain a large amount of n-11 gadoleic acid and/or cetoleic acid.

Examples of fatty acids other than MUFAs contained in fish oils and the like include saturated fatty acids (containing 14, 16, 18, 20 carbons, and the like), di- and triunsaturated fatty acids (containing 18, 20 carbons, and the like), and polyunsaturated fatty acids having a degree of unsaturation of 4 or greater (PUFAs, having 20, 22 carbons, and the like). Among these, polyunsaturated fatty acids are the fatty acids characteristic of fish oils and the like. For example, they are fatty acids having not less than 20 carbons and having not less than 4 double bonds. Specific examples include arachidonic acid (20:4, n-6), eicosapentaenoic acid (20:5, n-3), docosapentaenoic acid (22:5, n-6), docosahexaenoic acid (22:6, n-3), and the like.

In the present invention, an ester of a MUFA is an ester of a lower alcohol having from 1 to 3 carbons of the MUFA, and preferably an ester of ethanol of the MUFA.

The production method of free monounsaturated fatty acids or lower alcohol esters thereof having 20 and/or 22 carbons according to an aspect of the present invention comprises hydrolyzing or alcoholizing marine product raw material-derived oil and/or fat, to obtain free fatty acids or lower alcohol esters (also called "processing step" hereinafter); distilling the free fatty acids or lower alcohol esters, and reducing a concentration of fatty acids having not more than 18 carbons in the free fatty acids or lower alcohol esters (also called "distillation step" hereinafter); and fractionating fractions of free monounsaturated fatty acids or lower alcohol esters thereof having 20 and/or 22 carbons by reverse phase distribution column chromatography (also called "column step" hereinafter); and may include other steps depending on the case.

The method for obtaining crude oil from each marine product raw material may be any method. Taking saury crude oil as an example, it is normally collected by a method such as the following, similar to other fish oils. Whole saury or processing remains such as fish heads, skin, backbones, and viscera generated by fish processing are crushed, digested, and then squeezed to separate them into stickwater and squeezed fluid. The oil and/or fat obtained together with the stickwater are separated from the stickwater by centrifugal separation, to make saury crude oil.

In general, crude fish oil is made into refined fish oil through refinement processes such as a degumming process, deacidification, decoloration using activated clay or activated carbon, a washing process, a deodorizing process using steam distillation, and the like, depending on the raw material. This refined fish oil may also be used as the raw material of the present invention. In other words, the marine product raw material-derived oil and/or fat used in the method of an aspect of the present invention can be refined oil obtained by performing such general refinement processes of crude oil obtained from a marine product. For example, a refined oil obtained by performing at least one refinement process among a degumming process, a deacidification process, and a decoloration process of crude oil obtained from a marine product can be used as the marine product raw material-derived oil and/or fat.

The processing step in the method of an aspect of the present invention is a step of decomposing marine product raw material-derived oil and fat into a free fatty acid or a lower alcohol ester by hydrolysis or alcoholysis. In hydrolysis, water and a catalyst or enzyme such as an acid are added to the oil and fat and reacted, and fatty acids bonded to glycerin are freed. In alcoholysis, a lower alcohol having from 1 to 3 carbons, preferably ethanol, and a catalyst or enzyme are added to the oil and/or fat and reacted, and fatty acids and lower alcohol esters bonded to glycerin are produced. The desired fatty acid can be concentrated by separating the free fatty acids or lower alcohol esters from the glycerin.

The distillation step in the method on an aspect of the present invention is a step of distillation to reduce a concentration of fatty acids having not more than 18 carbons in the free fatty acids or lower alcohol esters produced in the processing step. Here, by removing as much of the fatty acids having not more than 18 carbons as possible, the subsequent column step can function effectively. The fatty acids having not more than 18 carbons are preferably reduced to not greater than 30% by area, not greater than 20% by area, not greater than 10% by area, not greater than 5% by area, or not greater than 1% by area, or in other words, not greater than 30% by weight, not greater than 20% by weight, not greater than 10% by weight, not greater than 5% by weight, or not greater than 1% by weight. As shown by the results of working examples in Tables 2 and 3, when the concentration of fatty acids having not more than 18 carbons is further reduced by distillation such as rectification, the C20:1 in the C20:1 fraction can be further concentrated in the column step.

The distillation method may be any method, but a method that can remove as much of the fatty acids having not more than 18 carbons as possible is preferred. Examples of such a distillation method include simple distillation such as molecular distillation and short path distillation, and rectification. Rectification is particularly preferred. Both rectification and simple distillation are preferably thin film distillation containing a thin-film heating evaporator.

In separating LC-MUFAs and fatty acids having not more than 18 carbons, separation is better by rectification than by simple distillation such as short path distillation or molecular distillation. For this reason, the amount of fatty acids having not more than 18 carbons can be efficiently reduced. The rectification conditions may be adjusted according to the fatty acid composition of the lower alcohol ester serving as the raw material. A preferred rectification condition is a column bottom temperature of not higher than 220° C., preferably from 150 to 220° C., and particularly preferably from 150 to 200° C. The reduced pressure condition is a pressure not higher than 10 mmHg, more preferably not higher than 1 mmHg, and even more preferably not higher than 0.1 mmHg. The lower limit of pressure is not particularly limited, and is set as appropriate depending on the equipment used. Various styles such as a packing style or tray style may be used in the interior structure for increasing the number of theoretical stages of separation, and a packing style that uses structured packing is more preferred. Simple distillation such as short path distillation and molecular distillation result in better productivity than rectification and are more suitable for large-scale processing. The preferred distillation condition in simple distillation, especially short path distillation or molecular distillation, is an evaporation surface temperature of not higher than 120° C., preferably from 50 to 120° C., and more preferably from 50 to 80° C. The preferred reduced pressure condition in simple distillation, especially short path distillation or molecular distillation, is a pressure of not higher than 0.05 mmHg, and more preferably not higher than 0.0013 mmHg. The lower limit of pressure is not particularly limited, and is set as appropriate depending on the equipment used.

The column step in the method of an aspect of the present invention is a step for concentrating MUFAs having 20 and/or 22 carbons or separating them from other unsaturated fatty acids. Reverse phase distribution column chromatography is suitable for separating MUFAs having 20 and/or 22 carbons from other unsaturated fatty acids. Specifically, an ODS column is preferred. The stationary phase is not particularly limited as long as it is a reverse phase distribution type of adsorption agent, and an ODS column which uses octadecylsilyl (ODS) is preferably used. The quantity of adsorption agent is preferably not less than 10 times and more preferably not less than 100 times the weight of raw material submitted to column chromatography. No particular limitation is placed on the upper limit of adsorption agent quantity, and for example, it may be 1000 times. As the eluate and the mobile phase, various polar solvents such as methanol, ethanol, 2-propanol, acetone, and acetonitrile may be used, or water-containing solvents obtained by adding water to these polar solvents may be used, and methanol is preferred.

By carrying out the above steps in order from the processing step to the column step, in other words, by carrying out distillation and chromatography, free MUFAs or lower alcohol esters thereof having 20 and/or 22 carbons can be concentrated to a high degree in all fatty acids. For example, they can be concentrated individually or in combination to a total of not less than 70% by weight, not less than 80% by weight, not less than 90% by weight, or not less than 95% by weight, and not greater than 99.99% by weight or not greater than 99.9999% by weight in all fatty acids.

By carrying out distillation and chromatography, the concentration of free fatty acids or lower alcohol esters thereof having not more than 18 carbons in all fatty acids can be reduced. For example, the concentration can be reduced individually or in combination to a total of not greater than 30% by weight, not greater than 20% by weight, not greater than 10% by weight, not greater than 5% by weight, or not greater than 1% by weight.

By carrying out distillation and chromatography, free saturated fatty acids or lower alcohol esters thereof can be reduced to not greater than 10% by weight, not greater than 5% by weight, or not greater than 1% by weight in all fatty acids.

By carrying out distillation and chromatography, PUFAs can be reduced to not greater than 10% by weight, not greater than 5% by weight, or not greater than 1% by weight in all fatty acids.

Because the obtained free fatty acids or lower alcohol esters thereof are obtained from oil and/or fat of marine products, the free monounsaturated fatty acids and lower alcohol esters thereof having 20 carbons which are concentrated to a high degree may be free gadoleic acid (n-11) and/or free gondoic acid (n-9) or lower alcohol esters thereof, and the free monounsaturated fatty acids and lower alcohol esters thereof having 22 carbons which are concentrated to a high degree may be free cetoleic acid (n-11) or lower alcohol esters thereof and/or free euricic acid (n-9) or lower alcohol esters thereof. The obtained free fatty acids or lower alcohol esters thereof may contain at least free gadoleic acid (n-11) or a lower alcohol ester thereof or free cetoleic acid (n-11) or a lower alcohol ester thereof, and may contain at least free gadoleic acid or a lower alcohol ester thereof.

Above all, the free fatty acids or lower alcohol esters thereof may contain free gadoleic acid or lower alcohol esters thereof in a concentration of not less than 30% by weight, not less than 40% by weight, not less than 50% by weight, not less than 60% by weight, or not less than 70% by weight in all fatty acids, and not more than 99.99% by weight or not more than 99.9999% by weight in all the fatty acids.

The free fatty acids or lower alcohol esters thereof may contain free cetoleic acid or lower alcohol esters thereof in a concentration of not less than 30% by weight, not less than 40% by weight, not less than 50% by weight, not less than 60% by weight, or not less than 70% by weight in all fatty acids, and not greater than 99.99% by weight or not greater than 99.9999% by weight in all the fatty acids.

The free fatty acids or lower alcohol esters thereof may contain free gondoic acid or lower alcohol esters thereof in a concentration of not less than 5% by weight, not less than 10% by weight, not less than 15% by weight, or not less than 20% by weight in all fatty acids, and not greater than 99.99% by weight or not greater than 99.9999% by weight in all the fatty acids. The free fatty acids or lower alcohol esters thereof may contain free euricic acid or lower alcohol esters thereof in a concentration of not less than 1% by weight, not less than 2% by weight, or not less than 3% by weight in all fatty acids, and not greater than 99.99% by weight or not greater than 99.9999% by weight in all the fatty acids.

When free gadoleic acid and free cetoleic acid or lower alcohol esters thereof are both present in the free fatty acids or lower alcohol esters thereof, the total concentration thereof may be not greater than 99.99% by weight or not greater than 99.9999% by weight in all fatty acids.

When two or more among free gadoleic acid, free cetoleic acid, free gondoic acid, and free euricic acid or lower alcohol esters thereof are present in the free fatty acids or lower alcohol esters thereof, the total concentration thereof may be not greater than 99.99% by weight or not greater than 99.9999% by weight in all the fatty acids.

Such free fatty acids or lower alcohol esters thereof are preferred as medicaments or dietary supplements having an LC-MUFA as an active ingredient.

Free fatty acids that can be produced according to an aspect of the present invention and contain MUFAs or lower alcohol esters thereof having 20 and/or 22 carbons which contain at least free gadoleic acid or a lower alcohol ester thereof or free cetoleic acid or a lower alcohol ester thereof in a concentration of at least 70% by weight in all the fatty acids may be preferably used as a medicament or dietary supplement having an LC-MUFA as an active ingredient.

Above all, the below free fatty acids or lower alcohol esters thereof according to an aspect of the present invention containing MUFAs having 20 and/or 22 carbons which contain at least free gadoleic acid or a lower alcohol ester thereof or free cetoleic acid or a lower alcohol ester thereof in a concentration of at least 70% by weight in all the fatty acids, not greater than 10% by weight of saturated fatty acids, and not greater than 5% by weight of PUFAs, or containing MUFAs having 20 and/or 22 carbons which contain at least free gadoleic acid or a lower alcohol ester thereof or free cetoleic acid or a lower alcohol ester thereof in a concentration of at least 90% by weight in all the fatty acids, not greater than 5% by weight of saturated fatty acids, and not greater than 1% by weight of PUFAs, are more preferred as medicaments or dietary supplements having LC-MUFAs as an active ingredient.

In medicaments in particular, free fatty acids or lower alcohol esters thereof containing MUFAs having 20 and/or 22 carbons which contain at least free gadoleic acid or a lower alcohol ester thereof or free cetoleic acid or a lower alcohol ester thereof in a concentration of at least 90% by weight in all the fatty acids, not greater than 1% by weight of saturated fatty acids, and not greater than 1% by weight of PUFAs are preferred.

In these free fatty acids or lower alcohol esters thereof, the concentration of free fatty acids or lower alcohol esters thereof having not more than 18 carbons among all the fatty acids may be, for example, individually or as a total in combination of not greater than 30% by weight, not greater than 20% by weight, not greater than 10% by weight, not greater than 5% by weight, or not greater than 1% by weight.

These high-purity compositions according to an aspect of the present invention are crucial to the research, development, and productization of isomers that can be obtained only from marine products like gadoleic acid (n-11) and cetoleic acid (n-11).

The free fatty acids or lower alcohol esters according to an aspect of the present invention contain at least gadoleic acid or cetoleic acid, and contain free monounsaturated fatty acids having 20 and/or 22 carbons in high concentration. Therefore, they are preferably applied to the research, development, and productization of isomers substances derived from marine products like gadoleic acid and/or cetoleic acid. In addition to the above, the free fatty acids or lower alcohol esters according to an aspect of the present invention are more preferably applied when the concentration of at least one fatty acid selected from the group consisting of fatty acids having not more than 18 carbons, saturated fatty acids, and polyunsaturated fatty acids is low.

The free fatty acids according to an aspect of the present invention may be used as salts thereof. Examples of salts include potassium salts and sodium salts.

As described above, the composition according to an aspect of the present invention contains LC-MUFAs in high concentration, and, depending on the case, the content of saturated fatty acids, LC-PUFAs, and the like can be greatly reduced. For this reason, it is extremely useful to use the composition in applications requiring LC-MUFAs in high concentration. Such applications are exemplified by foodstuffs, dietary supplements, medicaments, and the like. Use in applications with the goal of utilizing LC-MUFA functionality, such as metabolic syndrome amelioration and lifestyle-related disease prevention, is particularly preferred.

Another aspect of the present invention provides a method for ameliorating metabolic syndrome, including administering the composition according to an aspect of the present invention as a metabolic syndrome ameliorating agent in a dose effective in metabolic syndrome amelioration to a subject requiring metabolic syndrome amelioration.

Yet another aspect of the present invention includes a method for preventing lifestyle-related diseases, including administering the composition according to an aspect of the present invention as a lifestyle-related disease preventing agent in a dose effective in lifestyle-related disease prevention to a subject requiring lifestyle-related disease prevention. Examples of administration subject include humans, animals, and the like.

For example, compositions according to aspects of the present invention (a) to (c) below are used as a metabolic syndrome ameliorating agent or a lifestyle-related disease preventing agent in these amelioration methods or prevention methods.

(a) A composition comprising free fatty acids or lower alcohol esters thereof containing monounsaturated fatty acids or lower alcohol esters thereof having 20 and/or 22 carbons which contain at least free gadoleic acid (n-11) or a lower alcohol ester thereof or free cetoleic acid (n-11) or a lower alcohol ester thereof in a concentration of not less than 70% by weight, not less than 80% by weight, or not less than 90% by weight in all fatty acids;

(b) A composition comprising free fatty acids or lower alcohol esters thereof containing monounsaturated fatty acids having 20 and/or 22 carbons which contain at least free gadoleic acid or a lower alcohol ester thereof or free cetoleic acid or a lower alcohol ester thereof in a concentration of at least 70% by weight in all fatty acids, saturated fatty acids in a concentration of not greater than 10% by weight in all the fatty acids, and polyunsaturated fatty acids in a concentration of not greater than 5% by weight in all the fatty acids; and (c) A composition comprising free fatty acids or lower alcohol esters thereof containing monounsaturated fatty acids having 20 and/or 22 carbons which contain at least free gadoleic acid or a lower alcohol ester thereof or free cetoleic acid or a lower alcohol ester thereof in a concentration of at least 90% by weight in all the fatty acids, saturated fatty acids in a concentration of not greater than 5% by weight in all the fatty acids, and polyunsaturated fatty acids in a concentration of not greater than 1% by weight in all the fatty acids.

Fish-derived refined oils contain approximately 30% by weight of monounsaturated fatty acids or lower alcohol esters thereof having 20 and/or 22 carbons, and such fish-derived refined oils have a metabolic syndrome ameliorating effect (for example, refer to WO/2012/121080; Lipids (2011) Vol. 46, pp. 425-434; J. Agric. Food Chem., 2011, Vol. 59, pp. 7482-7489; Lipids in Health and Disease, 2011, Vol. 10, pp. 189-199; and the like). The metabolic syndrome ameliorating agent or lifestyle-related disease preventing agent according to an aspect of the present invention contains a higher concentration, for example, not less than 70% by weight, of free monounsaturated fatty acids or lower alcohol esters thereof having 20 and/or 22 carbons which contain at least free gadoleic acid or a lower alcohol ester thereof or free cetoleic acid or a lower alcohol ester thereof.

Thus, it can be expected to have a higher metabolic syndrome ameliorating effect or lifestyle-related disease preventing effect.

According to another aspect of the present invention, a metabolic syndrome ameliorating composition or a lifestyle-related disease preventing composition comprising the metabolic syndrome ameliorating agent or lifestyle-related disease preventing agent described in the above (a) to (c) and an additive is provided. When used as a medicament, examples of the additive include pharmaceutically acceptable bases, carriers, excipients, disintegrators, lubricants, and colorants. The metabolic syndrome ameliorating composition or lifestyle-related disease preventing composition according to another aspect of the present invention may be preferably provided as a soft capsule of gelatin or the like, or as a tablet or capsule after processing into powdered oil and/or fat. The metabolic syndrome ameliorating composition or lifestyle-related disease preventing composition may be produced by blending the metabolic syndrome ameliorating agent or lifestyle-related disease preventing agent of the above (a) to (c) and the additive in a prescribed blending ratio, and, as necessary, performing additional steps such as processing into the desired dosage form. The content ratio of metabolic syndrome ameliorating agent or lifestyle-related disease preventing agent in the metabolic syndrome ameliorating composition or lifestyle-related disease preventing composition is not particularly limited as long as it is a content ratio expected to have an effect. For example, it may be from 0.01% by weight to 100% by weight, from 0.1% by weight to 100% by weight, or from 3% by weight to 100% by weight.

The metabolic syndrome ameliorating agent or lifestyle-related disease preventing agent of the above (a) to (c) may each be used in foodstuffs as foodstuff base ingredients. The term "foodstuffs" means foodstuffs in general including beverages, and in addition to general foodstuffs including health foodstuffs such as dietary supplements, it includes food for specified health uses or food with nutrient function claims set forth in the health-promoting food regulations of the Consumer Affairs Agency. For example, it may be a functional foodstuff labeled as having a metabolic syndrome ameliorating action or labeled as having a lifestyle-related disease preventing action. When the metabolic syndrome ameliorating agents or lifestyle-related disease preventing agents of the above (a) to (c) are used as foodstuff base ingredients, the foodstuff containing them may be produced by combining them with other foodstuff base ingredients as necessary, and performing additional steps such as molding into any shape. The content ratio of the metabolic syndrome ameliorating agent or lifestyle-related disease preventing agent is not particularly limited, and may be a content ratio expected to have an effect. As foodstuff base ingredients, they may also be used as additives for animal feed in addition to foodstuffs.

When administered as a medicament or a foodstuff to an administration subject, the dosage may be set as appropriate according to the degree of symptoms and the age, weight, and health condition of the administration subject. For example, the present composition may be administered orally or parenterally in a dosage of 1 mg to 1 g/kg/day and preferably 5 mg to 300 mg/kg/day in adults, either once per day or divided into 2 to 4 or more doses at appropriate intervals.

In the present specification, in addition to an independent step, the term "step" also refers to a step that achieves an intended object of the step even when the step cannot be clearly distinguished from other steps.

In the present specification, numeric ranges indicated by "to" are ranges that include the minimum and maximum values each stated before and after the "to."

In the present specification, if multiple substances corresponding to each of the components in the composition are present, the amount of each component in the composition, unless otherwise noted, is taken to mean the total amount of these multiple substances present in the composition. In the present specification, the terms "not greater than" and "less than" in regard to percentages mean ranges including 0% or a value undetectable by present means, unless the lower limit is specifically stated.

In the present specification, use of the indefinite article "a" or "an" does not exclude the possibility that one or a plurality of elements exists, unless clearly indicated or associated in the context. Accordingly, the indefinite article "a" or "an" normally means "at least one."

In the present specification, the verb "comprising" and its conjugations are used in an unlimited sense and include the items following that word, and they mean that items not specifically mentioned are not excluded.

In the present specification, the features of each invention described in embodiments related to each aspect of the invention may be combined as desired to form new embodiments, and it is to be understood that such new embodiments may be included in each of the aspects of the present invention.

The present invention is described below in detail using Working Examples. However, the present invention is not limited in any manner by these Working Examples. Furthermore, unless indicated otherwise, "%" in the below described Working Examples is taken to mean "% by weight".

EXAMPLE

A composition of fatty acids may be determined by the normal method. Specifically, an analyte oil and fat is esterified using a lower alcohol and a catalyst to obtain fatty acid lower alcohol esters. Thereafter, the obtained fatty acid lower alcohol esters are analyzed using gas chromatography. Peaks corresponding to each of the fatty acids are identified in the obtained gas chromatography chart, and the peak area of each of the fatty acids is determined using the Agilent ChemStation integration algorithm (revision C.01.03 [37], Agilent Technologies). "Peak area" indicates a ratio of the peak area for a respective component to the area of all peaks as determined in charts analyzed by gas chromatography, thin-layer chromatography/flame ionization detector (TLC/FID) or the like of oil and fat having various fatty acids as constituent components, and indicates the content ratio of the component of the peak. The value according to the area percent obtained by the measurement method described above is the same as the value according to the weight percent of each fatty acid in a sample, and may be used interchangeably. Refer to "Basic Oil Analytical Test Methods", 2013 Edition, 2.4.2.1-2013 Fatty Acid Composition (FID constant temperature gas chromatograph method) and 2.4.2.2-2013 Fatty Acid Composition (FID heating gas chromatograph method) established by the Japan Oil Chemists' Society (JOCS).

The fatty acid composition was determined by gas chromatography by the method indicated in the Working Examples. A lipid composition was determined using TLC/FID. Detailed conditions are indicated in the Working Examples.

The ethyl esterification rate of the alkyl esterification method used in Working Examples has been empirically determined to be from 95% to 100%. Therefore, in sections of Working Examples, it was presumed that nearly all of saturated or unsaturated fatty acids contained in the obtained starting material ethyl ester were in a fatty acid ethyl ester form. Consequently, the saturated or unsaturated fatty acids contained in the samples are all described below as saturated or unsaturated fatty acids in the ethyl ester form. However, this does not completely negate the fact that fatty acids of a form other than a free fatty acid form or a lower alcohol ester form are included.

Working Example 1

Degumming, deacidification, and decoloration processes were performed on 4,000 kg of saury crude oil collected from fresh saury, and 3,520 kg of saury refined oil was obtained. 2,000 kg of the obtained saury refined oil was subjected to ethyl esterification by transesterification with sodium ethylate. Then, 0.5% of vitamin E was added as an antioxidant, and 1,999 kg of saury oil ethyl ester (sample A) was obtained. The analysis values of the obtained saury oil ethyl ester are shown in Table 1.

TABLE 1

| Item | Analysis value |
| --- | --- |
| Acid value | 0.19 |
| Peroxide value (meg/kg) | 1.5 |
| Gardner color scale | 4+ |
| The amount of fatty acids having not more than 18 carbons (%) | 43.6 |
| The amount of LC-PUFA (%) | 20.7 |
| C20:1 (%) | 12.6 |
| C22:1 (%) | 15.1 |
| Residual triglyceride (%) | ≤1% |

※0.5% of vitamin E was added as antioxidant
※The fatty acid composition (%) indicates a ratio of the peak area for a respective component to the area of all fatty acid peaks as determined in charts analyzed by gas chromatography.

Working Example 2

Refinement of Saury Oil Ethyl Ester by Rectification 100.06 g of saury oil ethyl ester was put in a 500 mL three-necked flask, and precision distillation was performed using a vacuum jacketed rectification column manufactured by Kiriyama Glass Co. (vacuum jacketed fractional distillation tube (Kiriyama Glass Co.), fractional distillation head (Kiriyama Glass Co.)) in which five pieces of laboratory packing EX (25 mm×50 mm, manufactured by Sulzer Chemtech Ltd.) were inserted. The conditions were: column bottom temperature 185° C., column bottom pressure 0.8 mmHg (approximately 107 Pa), column top-most pressure 8 Pa, and column top-most vapor temperature 133° C. As a result, 43.2 g of rectification fractions (sample B) and 54.5 g of rectification residue (sample C) were obtained. The fatty acid compositions of samples B and C are shown in Table 2.

Working Example 3

Refinement of Saury Oil Ethyl Ester by Molecular Distillation 905.5 g of saury oil ethyl ester was put into a centrifugal molecular distillation apparatus (MS-150) manufactured by Nippon Sharyo, Ltd., and distillation was performed at an evaporation surface temperature of 90° C. and pressure of 0.015 Torr, to yield 209.7 g of distillation fractions and 596.2 g of distillation residue (sample D). The fatty acid composition of sample D is shown in Table 2.

TABLE 2

|  | Sample B | Sample C | Sample D |
|---|---|---|---|
| Weight (g) | 43.2 | 54.5 | 596.2 |
| Fatty acid composition (%) |  |  |  |
| The amount of fatty acids having not more than 18 carbons | 90.1 | 0.0 | 26.0 |
| The amount of saturated fatty acid | 46.3 | 0.4 | 9.0 |
| The amount of LC-PUFA | 1.2 | 34.9 | 35.4 |
| C20:1 | 0.2 | 25.2 | 17.3 |
| C22:1 | 0.0 | 32.0 | 22.2 |

※The fatty acid composition (%) indicates a ratio of the peak area for a respective component to the area of all fatty acid peaks as determined in charts analyzed by gas chromatography.

Working Example 4

Refinement of LC-MUFAs by HPLC after Distillation

For samples C and D containing fatty acid ethyl esters refined by rectification or molecular distillation, a higher degree of refinement was additionally carried out by ODS (octadecylsilyl)-HPLC. The separation conditions are listed below.

Separation Conditions
Column: JAIGEL-ODS-AP-30, SP-120-15 (manufactured by Japan Analytical Industry Co., Ltd.), 30 φ×200 mm
Eluate: methanol
Flow rate: 20 mL/min
Column temperature: 40° C.
Sample load: 6.30 g
Detector: differential refractometer With the differential refractometer peak and hold time as indices, the fraction possibly containing C20:1 (called "C20:1 fraction" hereinafter) and the fraction possibly containing C22:1 (called "C22:1 fraction" hereinafter) were each fractionated from samples E to H below. The fatty acid composition of each fraction is shown in Table 3. The fatty acid compositions (%) are area ratios based on the chart of gas chromatograms as described above.

Sample E: sample in which the C20:1 fraction was fractionated with sample C as a raw material
Sample F: sample in which the C22:1 fraction was fractionated with sample C as a raw material
Sample G: sample in which the C20:1 fraction was fractionated with sample D as a raw material
Sample H: sample in which the C22:1 fraction was fractionated with sample D as a raw material

TABLE 3

|  | Sample E | Sample F | Sample G | Sample H |
|---|---|---|---|---|
| Sample load (g) | 6.300 | 6.300 | 6.300 | 6.300 |
| Recovered amount (g) | 1.211 | 1.799 | 0.907 | 0.704 |
| The fatty acid compositions (%) |  |  |  |  |
| The amount of fatty acids having not more than 18 carbons | 0.24 | 0.00 | 2.81 | 0.00 |
| The amount of saturated fatty acids | 0.24 | 0.94 | 3.58 | 1.17 |
| The amount of C20:1 | 95.70 | 14.53 | 27.30 | 0.00 |
| C20:1n11 | 73.65 | 11.33 | 21.28 | 0.00 |
| C20:1n9 | 20.69 | 3.02 | 5.67 | 0.00 |

TABLE 3-continued

|  | Sample E | Sample F | Sample G | Sample H |
|---|---|---|---|---|
| C20:1n7 | 1.36 | 0.18 | 0.35 | 0.00 |
| The amount of C22:1 | 0.15 | 83.41 | 67.88 | 91.08 |
| C22:1n11 | 0.15 | 78.81 | 64.06 | 86.26 |
| C22:1n9 | 0.00 | 3.48 | 2.89 | 3.63 |
| C22:1n7 | 0.00 | 1.12 | 0.92 | 1.19 |
| The amount of LC-MUFA | 95.85 | 97.94 | 95.18 | 91.08 |
| The amount of LC-PUFA | 0.00 | 0.00 | 0.00 | 1.16 |

As shown in Table 3, in all of the samples E to H, the content ratio of LC-MUFAs was increased by performing ODS-HPLC refinement. In particular, in samples E, F, and G, they were concentrated to a concentration of not less than 90% by weight.

On the other hand, when sample C, for which rectification was employed as the first refinement step, was used as a raw material, LC-MUFAs having 20 carbons could be concentrated to a higher degree after the rectification step (samples E, F) than when sample D, for which molecular distillation was employed, was used as a raw material. This is because only a small amount of fatty acids having not more than 18 carbons remained after the distillation step, and in the HPLC step, a decrease in separation efficiency of C20:1 due to the presence of fatty acids having not more than 18 carbons was effectively suppressed. It is understood that selecting the method of the initial distillation step is effective in increasing the C20:1 concentration. It was found that, for this reason, removing fatty acids having not more than 18 carbons and saturated fatty acids in a refinement step prior to HPLC refinement is effective for obtaining LC-MUFA ethyl esters containing a high concentration of C20:1.

Surprisingly, it was also found that LC-MUFAs become more highly concentrated by removing fatty acids having not more than 18 carbons and saturated fatty acids using rectification, and when sample E and sample G, which had the same concentration of LC-MUFAs, were compared, the recovery rate of LC-MUFAs was 1.34 times higher.

As demonstrated in the present examples, the compositions obtained by aspects of the present invention contain LC-MUFAs in high concentration, and the contents of saturated fatty acids and LC-PUFAs are extremely low. For this reason, it is extremely useful to use them in applications requiring LC-MUFAs in high concentration. Examples of such applications include applications for foodstuffs, dietary supplements, medicaments, and the like. Use in applications with the goal of utilizing LC-MUFA functionality, such as metabolic syndrome amelioration and lifestyle-related disease prevention, is particularly preferred.

Disclosure of Japanese Patent Application No. 2014-136436 filed on Jul. 2, 2014 is incorporated herein in its entirety by reference.

All documents, patent applications, and technical specifications stated in the present specification are incorporated by citation in the present specification to the same degree as if stated to be incorporated by reference specifically and individually.

The invention claimed is:
1. Free monounsaturated fatty acids or lower alcohol esters thereof having 20 and/or 22 carbons obtained by a method comprising
hydrolyzing or alcoholizing a marine product raw material-derived oil and/or fat, to obtain free fatty acids or lower alcohol esters thereof;

distilling the free fatty acids or lower alcohol esters thereof, and reducing a concentration of fatty acids having not more than 18 carbons in the free fatty acids or lower alcohol esters thereof; and fractionating fractions of free monounsaturated fatty acids or lower alcohol esters thereof having 20 and/or 22 carbons by reverse phase distribution column chromatography, wherein a concentration of free fatty acids or lower alcohol esters thereof having not more than 18 carbons is greater than zero but not greater than 5% by weight of all the fatty acids.

2. Free fatty acids or lower alcohol esters thereof comprising:

free monounsaturated fatty acids having 20 and/or 22 carbons which contain at least free gadoleic acid (n-11) or a lower alcohol ester thereof or free cetoleic acid (n-11) or a lower alcohol ester thereof in a concentration of not less than 70% by weight in all the fatty acids, wherein a concentration of free fatty acids or lower alcohol esters thereof having not more than 18 carbons is greater than zero but not greater than 5% by weight of all the fatty acids.

3. The free fatty acids or lower alcohol esters thereof according to claim 2, wherein the free monounsaturated fatty acid or lower alcohol ester thereof having 20 carbons comprises free gadoleic acid (n-11) or a lower alcohol ester thereof and/or free gondoic acid (n-9) or a lower alcohol ester thereof, and the free monounsaturated fatty acid or lower alcohol ester thereof having 22 carbons is free cetoleic acid (n-11) or a lower alcohol ester thereof and/or free euricic acid (n-9) and a lower alcohol ester thereof.

4. Free fatty acids or lower alcohol esters thereof, comprising:

free monounsaturated fatty acids or lower alcohol esters thereof having 20 and/or 22 carbons which contain at least free gadoleic acid or a lower alcohol ester thereof or free cetoleic acid or a lower alcohol ester thereof in a concentration of at least 70% by weight in all the fatty acids;

free saturated fatty acids or lower alcohol esters thereof in a concentration of greater than zero but not greater than 10% by weight in all the fatty acids; and free polyunsaturated fatty acids or lower alcohol esters thereof in a concentration of not greater than 5% by weight in all the fatty acids.

5. The free fatty acids or lower alcohol esters thereof according to claim 4, wherein the free monounsaturated fatty acids or lower alcohol esters thereof having 20 and/or 22 carbons which contain at least free gadoleic acid or a lower alcohol ester thereof or free cetoleic acid or a lower alcohol ester thereof in a concentration of at least 90% by weight in all the fatty acids, the free saturated fatty acids or lower alcohol esters thereof have a concentration of not greater than 5% by weight in all the fatty acids, and the free polyunsaturated fatty acids or lower alcohol esters thereof have a concentration of not greater than 1% by weight in all the fatty acids.

6. The free monounsaturated fatty acids or lower alcohol esters thereof according to claim 1, wherein the acids or esters comprise at least free gadoleic acid or a lower alcohol ester thereof, the free gadoleic acid (n-11) or a lower alcohol ester thereof has a concentration of not less than 30% by weight in all the fatty acids.

7. A foodstuff comprising the free monounsaturated fatty acids or lower alcohol esters thereof of claim 1.

8. A composition comprising the free monounsaturated fatty acids or lower alcohol esters thereof of claim 1 and a pharmaceutically acceptable additive.

* * * * *